United States Patent [19]
Gasser et al.

[11] Patent Number: 5,520,922
[45] Date of Patent: May 28, 1996

[54] FORMABLE COMPOSITION AND ITS USE AS FILLING MATERIAL FOR DENTAL ROOT CANALS

[75] Inventors: Oswald Gasser, Seefeld; Rainer Guggenberger, Herrsching, both of Germany

[73] Assignee: THERA Patent GmbH & Co. KG, Gesellschaft für industrielle Schutzrechte, Seefeld, Germany

[21] Appl. No.: 323,708

[22] Filed: Oct. 18, 1994

Related U.S. Application Data

[63] Continuation of Ser. No. 117,739, Sep. 8, 1993, abandoned, which is a continuation of Ser. No. 738,435, Jul. 31, 1991, abandoned.

[30] Foreign Application Priority Data

Jul. 31, 1990 [DE] Germany .......................... 40 24 322.2

[51] Int. Cl.⁶ .......................... A61K 6/027; A61K 6/083
[52] U.S. Cl. .......................... 424/422; 523/115; 523/116; 523/117; 424/617; 424/696; 524/403; 524/406; 524/413; 524/434; 524/539; 524/610
[58] Field of Search .......... 424/422, 9.4; 523/116–117; 106/35; 524/403, 406, 413, 432, 492, 539

[56] References Cited

U.S. PATENT DOCUMENTS

| | | | |
|---|---|---|---|
| Re. 33,100 | 10/1989 | Ibsen et al. | 106/35 |
| 3,814,717 | 6/1974 | Wilson et al. | 260/29.6 M |
| 4,016,124 | 4/1977 | Crisp et al. | 260/29.6 M |
| 4,137,086 | 1/1979 | Potter et al. | 106/52 |
| 4,143,018 | 3/1979 | Crisp et al. | 260/29.6 M |
| 4,209,434 | 6/1980 | Wilson et al. | 260/29.6 H |
| 4,376,835 | 3/1983 | Schmitt et al. | 523/16 |
| 4,569,954 | 2/1986 | Wilson et al. | 523/116 |
| 4,647,600 | 3/1987 | Kawahara et al. | 523/117 |
| 4,738,722 | 4/1988 | Ibsen et al. | 106/35 |
| 4,861,808 | 8/1989 | Billington et al. | 524/456 |
| 4,927,866 | 5/1990 | Purrmann et al. | 523/115 |
| 5,051,453 | 9/1991 | Okabayashi et al. | 523/116 |

FOREIGN PATENT DOCUMENTS

| | | |
|---|---|---|
| 0329268 | 8/1989 | European Pat. Off. . |
| 0340016 | 11/1989 | European Pat. Off. . |
| 2061513 | 1/1900 | Germany . |
| 2319715 | 8/1979 | Germany . |
| 3122067 | 3/1982 | Germany . |
| 3806448 | 2/1988 | Germany . |
| 3941629 | 6/1990 | Germany . |
| 3930921 | 7/1990 | Germany . |
| 1314090 | 4/1973 | United Kingdom . |
| 1532954 | 11/1978 | United Kingdom . |
| 2028855 | 5/1980 | United Kingdom . |
| WO80/00409 | 3/1980 | WIPO . |

OTHER PUBLICATIONS

Wilson et al, (1988), Glass–Ionomer Cement, Quintessence Publishing Co., Inc. pp. 21–50.
American Nat'l Standards/American Dental Assoc., (1983), Spec. No. 57 for Endodontic Filling Materials.

*Primary Examiner*—Edward J. Webman
*Attorney, Agent, or Firm*—Birch, Stewart, Kolasch & Birch

[57] ABSTRACT

There are provided formable compositions which comprise:

(A) 25 to 80% by weight of a glass ionomer cement, containing (a) an aluminum fluorosilicate glass, (b) at least one polymeric polyacid with an average molecular weight >500, (c) water and (d) optionally a chelating agent;

(B) and 20 to 75% by weight of a fluoride and/or oxide and/or mixed fluoride and/or mixed oxide of heavy metal elements which are essentially insoluble at ambient temperatures in an aqueous solution containing the polymeric polyacid and/or an aqueous solution containing the chelating agent.

The compositions are especially well suited as filling materials for dental root canals.

19 Claims, No Drawings

FORMABLE COMPOSITION AND ITS USE AS FILLING MATERIAL FOR DENTAL ROOT CANALS

This application is a continuation of application Ser. No. 08/117,739 filed on Sep. 8, 1993, now abandoned, which was a continuation of application Ser. No. 07/738,435, filed on Jul. 31, 1991, now abandoned.

FIELD OF THE INVENTION

The present invention provides a formable composition which can be used as a filling material for dental root canals.

BACKGROUND OF THE INVENTION

Due to events such as caries, loose fillings, trauma and infection, the pulpa (i.e., the dental pulp) of living teeth can often become inflamed. In most cases such inflammation is irreversible, and as a result the affected pulpa must be removed by a dentist. In addition to the pulpa, bordering infected hard tissues must also be removed. The cavities formed by the removal of such pulp and tissue (i.e., a root canal operation) must be tightly sealed. To achieve this end, there are marketed a number of products which comprise zinc oxide or calcium hydroxide in combination with an organic salt former. However, none of these marketed materials have completely or satisfactorily met the requirements of a root canal filling material.

Root canal filling materials must form tight seals in order to prevent an invasion into the canal of infectious germs. For example, after root canal operations, there is often a danger of maxillary infection. A high degree of histocompatibility is also required in a filling material, because the filling materials upon emerging from the dental root tip can come into contact with living tissue. Moreover, for maintaining tightness, the root canal filling materials should display only a very slight solubility. Finally, so as to allow for their introduction into narrow root canals, a suitable processing time and viscosity should also be possessed by the filling materials.

In order to increase the sealing tightness of filling materials previously utilized, and in order to compensate for shrinkage during hardening reactions, formable filling materials have frequently been used as sealants in combination with thin pegs made from gutta-percha (i.e., a filled, natural resin material). For example, in one textbook method, many such pegs are laterally condensed in a filling process, so as to keep the proportion of formable filling material used as low as possible. The method is extremely time consuming.

Glass ionomer cements are known for their ability to form tight edge seals (e.g., they display a chemicophysical adhesion to the dental substance). Furthermore, they show only very slight solubility and are categorized as histocompatible. Even so, they lack a sufficient processing time for introduction into a root canal. In conventional application areas for glass ionomer cements (e.g., dental fillings, securing cements, sealant materials and stump reconstruction materials) the cements' required processing times were only two to three minutes. For the filling of root canals (including the necessary X-ray check), however, a dentist needs about ten minutes of processing time. Additionally, the viscosities of the glass ionomer cements are often too high for their introduction into a root canal by conventional means. That is, the pastes formed therewith are too thick or solid. Moreover, when glass ionomer cement systems have been diluted, this has led to materials having high solubilities.

U.S. Pat. No. 4,861,808 discloses glass ionomer compositions which contain a light metal fluoride, namely strontium fluoride, which is used to make dental fillings X-ray visible. The X-ray opacity and the processability of the produced compositions are, however, not satisfactory.

U.S. Pat. No. Re. 33,100 describes glass ionomer compositions which, to prevent irritation of the dental pulp, are buffered with 5 to 20% by weight of a soluble heavy metal oxide, namely zinc oxide, and 0 to 10% by weight titanium dioxide. The processability of these compositions and the durability of dental fillings made therewith have not heretofore been satisfactory.

SUMMARY OF THE INVENTION

A goal of the present invention is to make available a root canal filling material which completely meets all the clinical requirements of such materials in an ideal fashion. For example, the provided materials should display an appropriate processing time, and provide tight fillings which display high mechanical strength and which possess at most only a very slight solubility.

Surprisingly, it has been discovered by the present inventors that suitable root canal filling materials which possess the above properties can be obtained by adding certain heavy metal compounds to a glass ionomer cement. More specifically, as a root canal filling material the present invention provides a formable composition comprising components (A) and (B) as follows:

(A) 25 to 80% by weight of a glass ionomer cement, containing:
  (a) an aluminum fluorosilicate glass,
  (b) at least one polymeric polyacid with an average molecular weight >500,
  (c) water, and
  (d) optionally a chelating agent; and (B) 20 to 75% by weight of a fluoride, an oxide, a mixed fluoride or a mixed oxide of heavy metal elements, or mixtures thereof, which are essentially insoluble in an aqueous solution containing the polymeric polyacid and in an aqueous solution containing the chelating agent.

Components (A) and (B) are preferably present in the filling materials in quantities of 35 to 65% by weight, post preferably in an amount of 50 to 65% by weight.

Surprisingly, despite the presence of such large amounts of inert heavy metal compounds (i.e., despite the heavy metals' presence reducing the proportion of reactive glass in the compositions), a filling material having good mechanical strength and only a slight solubility is obtained. Moreover, the compositions display a flowability which is well suited to forming a root canal filling material. In addition, the processing time of the compositions is increased in a desirable way, (i.e., better processability) without also creating any significant concessions with regard to solubility or mechanical strength.

DETAILED DESCRIPTION OF THE INVENTION

The calcium aluminum fluorosilicate glasses described in DE-A-20 61 513 and EP-A-O 023 013 and the strontium aluminum fluorosilicate glasses described in EP-A-0 241 277 can be used as constituent (a) of component (A) in the present inventive filling materials. The aluminum fluorosilicate glass powders used in the present invention preferably consist of, in addition to oxygen, the following:

| Constituent | Calculated as | % by weight |
|---|---|---|
| Si | $SiO_2$ | 10–60 |
| Al | $Al_2O_3$ | 10–50 |
| Ca | CaO | 0–40 |
| Sr | SrO | 0–40 |
| F | F | 1–40 |
| Na | $Na_2O$ | 0–10 |
| P | $P_2O_5$ | 0–10 | at least 1% by weight of CaO and/or SrO are contained therein, and in total 0 to 30% by weight, calculated as oxides, of B, Bi, Zn, Mg, Sn, Ti, Zr, La or other trivalent lanthanoids, K, W, Ge, as well as further additives which do not impair the properties of the glass powders and are physiologically acceptable. The glass can be made X-ray visible if desired by adding 10 to 30% by weight of $La_2O_3$ thereto.

The powder particles more preferably comprise:

| | |
|---|---|
| Si as $SiO_2$ | 20–50% by weight |
| Al as $Al_2O_3$ | 10–40% by weight |
| Ca as CaO | 0–35% by weight |
| Sr as SrO | 0–35% by weight |
| F | 5–30% by weight |
| Na as $Na_2O$ | 0–8% by weight |
| P as $P_2O_5$ | 1–10% by weight | wherein 0 to 30% by weight of Ca (calculated as CaO) and/or Sr (calculated as SrO) are contained therein, and in total 0 to 10% by weight of $B_2O_3$, $Bi_2O_3$, ZnO, MgO, $SnO_2$, $TiO_2$, $ZrO_2$, $La_2O_3$ or other oxides of trivalent lanthanoids, $K_2O$, $WO_3$, $GeO_2$, as well as further additives which do not impair the glass properties of the glass powders and are physiologically acceptable.

Most preferably, the glass powders used herein contain the following:

| | |
|---|---|
| Si as $SiO_2$ | 20–40% by weight |
| Al as $Al_2O_3$ | 15–35% by weight |
| Ca as CaO | 5–25% by weight |
| F | 10–30% by weight |
| Na as $Na_2O$ | 1–8% by weight |
| P as $P_2O_5$ | 1–10% by weight |
| La as $La_2O_3$ | 0–30% by weight |

The glass powders used in the present invention preferably have a minimum average particle size (weighted average) of at least 1 μm and more preferably at least 3 μm. Their average particle size (weighted average) is preferably 1–20 μm, more preferably 3–15 μm and most preferably 3–10 μm. The particles preferably have a maximum particle size of 150 μm, more preferably 100 μm, and most preferably 60 μm.

The powders used in the present invention are optionally subjected to a surface treatment as per European Patent 0 023 013. To this end, the glass powders are treated on their surface with acid, preferably at room temperature. Acid-group-containing substances are used, e.g., hydrochloric acid, sulfuric acid, nitric acid, acetic acid, propionic acid or perchloric acid, which form soluble calcium salts or strontium salts. The acids are preferably used in a concentration of 0.01 to 10% by weight, more preferably in a concentration of 0.05 to 3% by weight. After the corresponding reaction time, the powders are separated from the solution and thoroughly washed so that after washing, practically no soluble calcium or strontium salts are located on the surface of the powder particles.

The polymeric polyacids which are used as the constituent (A)'s component (b) can, for example, be polycarboxylic acids such as those previously known in the preparation of glass ionomer cement powders (e.g., polymaleic acid, polyacrylic acid, polyitaconic acid and mixtures thereof or copolymers thereof, particularly the maleic acid/acrylic acid copolymers and/or acrylic acid/itaconic acid copolymers known from EP-A-0 024 056). The average molecular weight of the polycarboxylic acids used in the present invention is more than 500. An average molecular weight of 1,000 to 20,000 is thought to be preferable, and from 3,000 to 10,000 is thought to be especially preferable. The polyacid is preferably used in concentrations of 5 to 50% by weight, relative to the amount of constituent (A)'s component (a).

Also suitable as a polymeric polyacid in the present invention are polyphosphonic acids, e.g., polyvinylphosphonic acid. These polyphosphonic acids can completely or partially replace the above described polycarboxylic acids.

Constituent (A)'s component (c), i.e. water, is used in quantities of 5 to 70% by weight, preferably 15 to 40% by weight, relative to the total mass of the constituent (A).

A chelating agent, such as is described in DE-A-23 19 715, can be contained as constituent (A)'s component (d). Tartaric acid is preferably used as the chelating agent. The chelating agent can be used in concentrations of 0.1 to 10, preferably 3 to 8% by weight, relative to the total mass of the constituent (A).

In order to obtain a glass ionomer cement having high storage stability prior to application, it is thought advisable to add preservatives thereto (e.g., benzoic acid or the like). The preservative(s) are preferably added to a dry polyacid component of the compositions. However, the same is not mandatory.

Additives for regulating the compositions' viscosity (e.g., pyrogenic silicic acid or the like) and for coloring (pigments) may be used if desired. Suitable concentrations of such ingredients are 0.1 to 10% by weight, preferably 1 to 5% by weight, relative to the total mass of the constituent (A).

The heavy metal compound present as component (B) is physiologically acceptable and inert, i.e., it is largely insoluble in the polymeric polyacids such as are used for glass ionomer cements, and it is selected from the group consisting of fluorides and/or oxides and/or mixed oxides and/or mixed fluorides of heavy metal elements which are essentially insoluble in an aqueous solution containing the polyacid and in an aqueous solution containing the chelating agent. Preferably, the selected heavy metal compounds should be essentially insoluble at ambient temperatures in an aqueous solution containing 30 to 50% w/w of the polymeric polyacid and/or in an aqueous solution containing 10 to 15% w/w of the chelating agent. Moreover, it is also preferable that the selected heavy metal elements should display a specific density of ca.>4. Preferred as constituent (B) heavy metal compounds are oxides/fluorides of the rare earth metals and the sixth sub-group of the periodic chart. Especially preferred as heavy metal compounds are those selected from the group consisting of yttrium fluoride, zirconium dioxide, lanthanum oxide, calcium tungstate and strontium tungstate. Quite especially preferred is calcium tungstate. The average particle sizes of the heavy metals are preferably between 0.5 μm and 20 μm, more preferably between 2 μm and 10 μm.

The compositions according to the present invention are preferably presented in a capsule which contains a powder and a fluid portion which are initially separated. Thereafter the powder and liquid portions are brought together, and a composition of the present invention is prepared by mechanical mixing with a usual mixing device.

An application capsule such as taught in EP-A-O 157 121 is preferably used. Such a capsule is also preferably provided with a small plastic tube as per DE-GM 90 03 983.1. With such a tube, the direct application of a mixed composition according to the invention into the root canal is possible.

The starting components of the inventors' compositions (powder and liquid) are preferably provided in a sterile form. The sterilization of such components can take place by heat treatment, sterile filtration (liquid) or particularly by gamma radiation.

The essential constituents of the glass ionomer cements used herein are:

| (A) | (a) | glass powder, |
| (A) | (b) | polymeric polyacid, |
| (A) | (c) | water, |
| (A) | (d) | chelating agent, and |
| (B) |     | heavy metal compound; | and can be divided in various ways such as follows:

Powder Component (A) (a) + B
(A) (a) + B + (A) (b)
(A) (a) + B + (A) (b) + (A) (d)

Liquid Component (A) (b) + (A) (c) + (A) (d)
(A) (c) + (A) (d)
(A) (c)

Paste/paste divisions are also possible, in which, for example, combinations with component (A)'s constituent (c) would be possible.

The following Examples illustrate the advantageous properties of the present inventive compositions.

EXAMPLE 1

A cement powder according to the present invention is prepared by intimately mixing the following ingredients together:

(1) 75 g of calcium tungstate;
(2) 25 g of calcium aluminum fluorosilicate glass of the following composition:
   7% by weight aluminum fluoride,
   13% by weight aluminum oxide,
   12% by weight aluminum phosphate,
   20% by weight calcium fluoride,
   4% by weight cryolite,
   20% by weight lanthanum oxide,
   24% by weight quartz*; and (3) 4 g of pyrogenic silicic acid and pigments.

*Average particle size 8 µm. Treated for one hour with a 10-fold amount of 0.2% hydrochloric acid, dried and heated for 6 hours at 400° C.

In addition, a cement liquid was prepared by dissolving 35 g of a copolymer (1:1) comprising acrylic acid and maleic acid (average molecular weight ca. 8,000 Dalton) and 11.8 g tartaric acid in 53.2 g distilled water.

The above cement powder (300 mg) was homogeneously mixed with 100 mg of the above cement liquid, using a spatula. The viscosity of the obtained mixture was well suited for introducing the prepared material into a root canal with a Lentulo (a spiral-shaped introduction device). A X-ray check shows the filled-in cement to be homogeneous, edge-tight and void-free. The cement can be processed satisfactorily and shows good adhesion to dental material. Physical data relating to the material are contained in Table 1, below.

EXAMPLE 2

The calcium tungstate in the cement powder according to Example 1 is replaced by 65 g zirconium dioxide (average particle size 6 µm). Thereafter, a satisfactory processing is carried out as described in Example 1. The cement obtained is introduced into a root canal. Physical data relating to the material are provided in Table 1.

EXAMPLE 3

100 mg of the liquid from Example 1 were welded into a small film sachet and attached to an application capsule as per EP-A 0 157 121, the main chamber of which is filled with 300 mg of the cement powder prepared in Example 1. A small application tube according to DE-GM G 90 03 983.1 is attached to the tip of the application capsules' movable nozzle. The capsule is welded into a blister film and sterilized with gamma rays. After mixing in a mechanical mixer (ESPE Capmix, duration of mixing 10 seconds), the cement, which corresponds in its properties to the material according to Example 1, can be directly applied into the root canal.

COMPARATIVE EXAMPLE 1

A root canal filling material based on zinc oxide/propionyl/acetophenone (Diaket®, ESPE), which is on the market, was mixed according to the manufacturer's instructions and processed. Physical data relating thereto are given in Table 1.

COMPARATIVE EXAMPLE 2

A cement is prepared corresponding to Example 1. However, unlike Example 1, the powder comprises only the described calcium aluminum fluorosilicate glass without the heavy metal compound according to the invention. See Table 1.

TABLE 1

| | Physical Properties | | | |
| --- | --- | --- | --- | --- |
| | Example 1 | Example 2 | Comparative Example 1 | Comparative Example 2 |
| Processing time (23° C.)[1] | 11 min. | 9:30 min. | 10 min. | 4 min. |
| Setting time (36° C.)[1] | 10:30 min. | 10 min. | 135 min. | 4:30 min. |
| Solubility[2] | 0.4% | 0.6% | 0.5% | 0.3% |

TABLE 1-continued

| | Physical Properties | | | |
|---|---|---|---|---|
| | Example 1 | Example 2 | Comparative Example 1 | Comparative Example 2 |
| Compressive strength[2] | 90 MPa | 82 MPa | <10 MPa | 95 MPa |
| X-ray visibility[1] | 9 mm Al | 8 ml Al | 5 mm Al | 3 mm Al |
| Viscosity[1] | 32 mm | 33 mm | 32 mm | 25 mm |

[1] Measurement as per ADA No. 57
[2] Measurement as per ISO 7489

By comparing the physical properties of the Examples and Comparative Examples in Table 1, the following can be concluded:

The root filling materials according to the invention display an advantageously long processing time which cannot be achieved by a glass ionomer cement without additive (Comparative Example 2). The setting time is nevertheless relatively quick. For example, it is considerably quicker than with root canal filling materials already on the market (Comparative Example 1).

Despite the high content of the inert heavy metal compounds in the inventive compositions, their solubility and compressive strength are virtually unchanged vis-a-vis a pure glass ionomer cement (Comparative Example 2). Moreover, the compressive strength clearly lies above the current level of known root canal fillers (Comparative Example 1).

The viscosity of the compositions according to the present invention are clearly improved vis-a-vis pure glass ionomer cements. The improvement is of great importance in practical applications precisely because only an adequate flowability permits a homogeneous filling-in of a narrow root canal to occur.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims. Each of the publications and patents referred herein above are expressly incorporated herein by reference in their entirety.

What is claimed is:

1. A formable composition comprising
   (A) 25 to 80% by weight of a glass ionomer cement, containing
      (a) an aluminum fluorosilicate glass having a weighted average particle size of 1–20 μg,
      (b) at least one polymeric polyacid with an average molecular weight >500, in an amount of 5 to 50% by weight based on the amount of the aluminum fluorosilicate glass,
      (c) water, and
   (B) 20 to 75% by weight of a fluoride, an oxide, a mixed fluoride or a mixed oxide of a heavy metal element, or mixtures thereof, which is essentially insoluble in an aqueous solution containing the polymeric polyacid, and which has an average particle size of 0.5 to 20 μg.

2. A formable composition as recited in claim 1, wherein the component (A) glass ionomer cement further comprises a constituent (d) chelating agent present in an amount of 0.1 to 10% by weight, based on the total weight of (A), and wherein the component (B) is essentially insoluble in an aqueous solution containing the chelating agent.

3. A formable composition as recited in claim 1 or 2, wherein component (A) is present in a quantity of 35 to 65% by weight, and component (B) is present in a quantity of 35 to 65% by weight.

4. A formable composition as recited in claim 1 or 2, wherein the component (B) heavy metal element is a rare earth metal or a metal of the sixth sub-group of the periodic chart.

5. A formable composition as recited in claim 1 or 2, wherein the component (B) heavy metal element is yttrium fluoride, zirconium dioxide, lanthanum oxide, calcium tungstate or strontium tungstate.

6. A formable composition as recited in claim 1, which is present in at least 2 part-compositions that are spatially separated from each other.

7. A formable composition as recited in claim 2, which is present in at least 2 part-compositions that are spatially separated from each other.

8. A formable composition as recited in claim 6, wherein at least one of the part-compositions is present in a solid form and at least one part-composition is present in a liquid or a paste form.

9. A formable composition as recited in claim 7, wherein at least one of the part-compositions is present in a solid form and at least one of the part-compositions is present in a liquid or a paste form.

10. A formable composition as recited in claim 8, wherein the solid part-composition contains the constituents (a) an aluminum fluorosilicate glass and 20 to 75% by weight of a fluoride, an oxide, a mixed fluoride or a mixed oxide of a heavy metal element, or mixtures thereof which is essentially insoluble in an aqueous solution containing the polymeric polyacid, and the liquid part-composition contains the constituents (b) at least one polymeric polyacid with an average molecular weight >500, and (c) water.

11. A formable composition as recited in claim 9, wherein the solid part-composition contains the constituents (a) an aluminum fluorosilicate glass and 20 to 75% by weight of a fluoride, an oxide, a mixed fluoride or a mixed oxide of a heavy metal element, or mixtures thereof which is essentially insoluble in an aqueous solution containing the polymeric polyacid, and the liquid part-composition contains the constituents (b) at least one polymeric polyacid with an average molecular weight >500, water and (d) a chelating agent.

12. A formable composition as recited in claim 8, wherein the solid part-composition contains the constituents (a) an aluminum fluorosilicate glass, (b) at least one polymeric polyacid with an average molecular weight =500, and 20 to 75% by weight of a fluoride, an oxide, a mixed fluoride or a mixed oxide of a heavy metal element, or mixtures thereof, which is essentially insoluble in an aqueous solution containing the polymeric polyacid, and the liquid part-composition contains the constituents (c) water and (d) a chelating agent.

13. A formable composition as recited in claim 9, wherein the solid part-composition contains the constituents (a) an aluminum fluorosilicate glass, (b) at least one polymeric polyacid with an average molecular weight >500, and 20 to 75% by weight of a fluoride, an oxide, a mixed fluoride or a mixed oxide of a heavy metal element, or mixtures thereof, which is essentially insoluble in an aqueous solution containing the polymeric polyacid, and the liquid part-composition contains the constituents (c) water and (d) a chelating agent.

14. A formable composition as recited in claim 8, wherein the solid part-composition contains the constituents (a) an aluminum fluorosilicate glass, (b) at least one polymeric polyacid with an average molecular weight >500, and 20 to 75% by weight of a fluoride, an oxide, a mixed fluoride or a mixed oxide of a heavy metal element, or mixtures thereof, which is essentially insoluble in an aqueous solution containing the polymeric polyacid, and the liquid part-composition contains the constituent (c) water.

15. A formable composition as recited in claim 9, wherein the solid part-composition contains the constituents (a) an aluminum fluorosilicate glass, (b) at least one polymeric polyacid with an average molecular weight >500, (d) a chelating agent and 20 to 75% by weight of a fluoride, an oxide, a mixed fluoride or a mixed oxide of a heavy metal element, or mixtures thereof, which is essentially insoluble in an aqueous solution containing the polymeric polyacid, and the liquid part-composition contains the constituent (c) water.

16. A formable composition as recited in claim 1 or 2, wherein the composition is a filling material for dental root canals.

17. A formable composition as recited in claim 1 or 2, wherein component (A) is present in a quantity of 50 to 65% by weight, and component (B) is present in a quantity of 50 to 65% by weight.

18. A formable composition as recited in claim 1 or 2, wherein the average molecular weight of the polymeric polyacid is from 3,000 to 10,000.

19. A formable composition as recited in claim 1, wherein the aluminum fluorosilicate glass is pretreated at its surface with an acid-group containing substance which can form soluble calcium salts or strontium salts, and thereafter the glass is thoroughly washed so that practically no soluble calcium or strontium salts are located on the surface of the glass.

* * * * *